US011925426B2

(12) United States Patent
Frasier et al.

(10) Patent No.: US 11,925,426 B2
(45) Date of Patent: Mar. 12, 2024

(54) SURGICAL ROBOT WITH ANTI-SKIVE FEATURE

(71) Applicant: DePuy Synthes Products, Inc., Raynham, MA (US)

(72) Inventors: William J Frasier, New Bedford, MA (US); Robert Brik, Brookline, MA (US); Richard Patrick Courtis, Dorchester, MA (US); Tarik Yardibi, Wayland, MA (US); Marc Puls, Thörigen (CH); Matias De La Fuente Klein, Aachen (DE); Lukas Theisgen, Aachen (DE); Manuel Vossel, Aachen (DE); Klaus Radermacher, Stolberg (DE)

(73) Assignee: DePuy Synthes Products, Inc., Raynham, MA (US)

( * ) Notice: Subject to any disclaimer, the term of this patent is extended or adjusted under 35 U.S.C. 154(b) by 300 days.

(21) Appl. No.: 17/377,953

(22) Filed: Jul. 16, 2021

(65) Prior Publication Data

US 2023/0020249 A1 Jan. 19, 2023

(51) Int. Cl.
*A61B 34/30* (2016.01)
*A61B 17/16* (2006.01)
*A61B 17/17* (2006.01)

(52) U.S. Cl.
CPC .......... *A61B 34/30* (2016.02); *A61B 17/1615* (2013.01); *A61B 17/1626* (2013.01); *A61B 17/17* (2013.01)

(58) Field of Classification Search
CPC . A61B 17/16; A61B 17/1613; A61B 17/1615; A61B 17/1617; A61B 17/162;
(Continued)

(56) References Cited

U.S. PATENT DOCUMENTS

| 5,807,378 A | 9/1998 | Jensen et al. |
| 5,921,987 A | 7/1999 | Stone et al. |

(Continued)

FOREIGN PATENT DOCUMENTS

| EP | 3351202 A1 * | 7/2018 | ......... A61B 17/1757 |
| EP | 3354223 A1 * | 8/2018 | ......... A61B 17/1615 |

(Continued)

OTHER PUBLICATIONS

"High Performance Instrument Systems and Accessories, Product Catalog", www.anspach.com, 2007, 28 pages.
(Continued)

*Primary Examiner* — Eric S Gibson
(74) *Attorney, Agent, or Firm* — Condo Roccia Koptiw LLP

(57) ABSTRACT

Systems, methods, and devices are disclosed for surgical instruments, systems, and methods for preventing skiving of a drilling instrument during a robotic or robot-assisted surgery are disclosed. In one embodiment, a scan of a patient's anatomy can be performed to produce a model of the bone to be drilled into and analysis of the surface can determine if the curvature is such that, if a target trajectory for a bore were followed, skiving of the drilling instrument is likely. If so, an alternate anti-skiving trajectory can be determined. The anti-skiving trajectory of a bore differs from the target trajectory by at least one of entry point, diameter, axis, or depth.

20 Claims, 10 Drawing Sheets

(58) Field of Classification Search
CPC ............ A61B 17/1622; A61B 17/1624; A61B 17/1626; A61B 17/1628; A61B 17/1671; A61B 34/10; A61B 34/20; A61B 34/30; A61B 2034/101; A61B 2034/102; A61B 2034/104; A61B 2034/105; A61B 2034/107; A61B 2034/2046; A61B 2034/2055; A61B 2034/2057; A61B 2034/305; A61B 2034/306

See application file for complete search history.

(56) References Cited

U.S. PATENT DOCUMENTS

| | | | |
|---|---|---|---|
| 6,725,080 | B2 | 4/2004 | Melkent et al. |
| 9,739,093 | B2 | 8/2017 | Trinh et al. |
| 9,782,229 | B2 | 10/2017 | Crawford et al. |
| 10,076,385 | B2 | 9/2018 | Shoham et al. |
| 10,231,790 | B2 | 3/2019 | Quaid et al. |
| 10,357,257 | B2 | 7/2019 | Kostrzewski et al. |
| 10,646,280 | B2 | 5/2020 | Crawford et al. |
| 10,765,438 | B2 * | 9/2020 | Kostrzewski ............ A61C 3/02 |
| 10,806,471 | B2 | 10/2020 | Chappuis et al. |
| 10,864,057 | B2 * | 12/2020 | Chappuis ............... A61B 34/30 |
| 10,874,466 | B2 | 12/2020 | Crawford et al. |
| 10,945,742 | B2 | 3/2021 | Kostrzewski et al. |
| 11,058,437 | B2 | 7/2021 | Capote et al. |
| 11,464,577 | B2 * | 10/2022 | Bush, Jr. .............. A61B 17/162 |
| 11,534,179 | B2 * | 12/2022 | Kostrewski ........... A61B 17/162 |
| 2004/0106916 | A1 | 6/2004 | Quaid et al. |
| 2007/0293867 | A1 | 12/2007 | Anitua et al. |
| 2015/0196365 | A1 | 7/2015 | Kostrzewski et al. |
| 2017/0079727 | A1 | 3/2017 | Crawford et al. |
| 2017/0224358 | A1 * | 8/2017 | Kostrzewski ........... A61B 34/30 |
| 2017/0239007 | A1 | 8/2017 | Crawford et al. |
| 2017/0245951 | A1 | 8/2017 | Crawford et al. |
| 2017/0312039 | A1 | 11/2017 | Crawford et al. |
| 2018/0014891 | A1 | 1/2018 | Krebs et al. |
| 2018/0110573 | A1 * | 4/2018 | Kostrzewski .......... B25J 15/0019 |
| 2018/0157238 | A1 | 6/2018 | Gogarty et al. |
| 2018/0199951 | A1 * | 7/2018 | Chappuis ............ A61B 17/7085 |
| 2018/0200016 | A1 * | 7/2018 | Chappuis ............... A61B 34/30 |
| 2018/0289432 | A1 * | 10/2018 | Kostrzewski .......... A61B 34/30 |
| 2019/0083191 | A1 | 3/2019 | Gilhooley et al. |
| 2019/0269469 | A1 * | 9/2019 | Bush, Jr. ................ A61B 34/76 |
| 2020/0222116 | A1 * | 7/2020 | Yadav ................ A61B 17/1637 |
| 2020/0289133 | A1 | 9/2020 | Elbanna et al. |
| 2020/0357508 | A1 * | 11/2020 | Deleu .................... G16H 50/50 |
| 2021/0022750 | A1 * | 1/2021 | Kostrewski ............ A61B 34/20 |
| 2021/0100567 | A1 | 4/2021 | Sharifi-Mehr et al. |
| 2023/0020249 | A1 * | 1/2023 | Frasier ............... A61B 17/1626 |

FOREIGN PATENT DOCUMENTS

| | | | | |
|---|---|---|---|---|
| EP | 3431025 | A1 | 1/2019 | |
| JP | 2018114273 | A * | 7/2018 | ......... A61B 17/1615 |
| JP | 2018114283 | A * | 7/2018 | ......... A61B 17/1757 |
| WO | WO2008016872 | A2 | 2/2008 | |
| WO | WO2010076385 | A1 | 7/2010 | |
| WO | WO2016087539 | A1 | 6/2016 | |
| WO | WO-2017121874 | A2 * | 7/2017 | ......... A61B 17/1615 |

OTHER PUBLICATIONS

"Click'X System. The complete top-loading pedicle screw and rod system for the posterior stabilization of the lower back", Synthes, www.synthes.com, 2007, 52 pages.

"Prodisc-C. Modular intervertebral disc prosthesis for restoring disc height and segmental motion in the cervical spine", Synthes, www.synthesprodisc.com, 2007, 36 pages.

Tofuku, et al., "Cervical Pedicle screw insertion using a gutter entry point at the transitional area between the lateral mass and lamina" Europe Spine Journal 2012, 6 pages.

Ortmaier, et al., "Experiments on robot assisted navigated drilling and milling of bones for pedicle screw placement", International Journal f Medical Robotics and computer Assisted Surgery, 2006, 14 pages.

Chung, et al., "An Image-Guided Robotic Surgery System for Spinal Fusion", International Journal of Control, Automation, and Systems, vol. 4, No. 1, Feb. 2006, 13 pages.

* cited by examiner

SURGICAL ROBOT WITH ANTI-SKIVE FEATURE

BACKGROUND

Surgical procedures are used to treat and cure a wide range of diseases, conditions, and injuries. For example, spinal surgeries often require precision drilling and placement of screws or other implants in bone or hard tissue. Improper drilling or maneuvering of the body during spinal surgery can be undesirable, for example, due to the proximity of the spinal cord and arteries. Further, accurate placement of screws and other implants can be important for a successful outcome. For example, spinal fusion is often augmented by stabilizing the vertebrae with fixation devices, such as metallic screws, rods, and plates, to facilitate bone fusion. In spinal fusion, as well as other surgeries, the accuracy with which the screws and other implants are placed in the bone can have a direct effect on the outcome of the procedure.

An increasingly common type of procedure is a robotic or robot-assisted surgical procedure, in which a surgical robot can guide or control one or more surgical instruments, such as a saw, drill, etc. In such procedures, the surgical robot can be coupled to an operating table or other operating room structure using a support and, in some embodiments, the support can be configured to selectively allow movement of the robot to a desired position. Accurate tracking of positions of the surgical instruments used in the system can be achieved using a variety of surgical navigation tracking systems. Robot assisted surgery can be advantageous because it can provide increased precision and accuracy with regard to the placement of surgical instruments during a procedure and the ability to follow a predetermined surgical plan.

However, initial precision and accuracy are of little use if undesirable movements occur during operation of a surgical robot. One such undesirable movement that can be difficult to track is skiving of a drilling instrument during operation, when the drill's tip deviates from its intended trajectory and results in a misplaced bore. Skiving can occur, for example, during the initiation of a drilling operation when a drill tip is set at an entry point in an angled fashion, such that the tip can deflect, "walk," or otherwise move itself away from the intended entry point before drilling into the material. In some cases, such skiving can result in movements off a planned trajectory that are too small for a surgical navigation tracking system to detect, but that are nonetheless undesirable because they can result in, for example, pedicle breach or compromised screw purchase in the context of spine surgery. Risk of skiving can be increased when, as in many surgical procedures, drilling is performed at predetermined desired trajectories on curved anatomical surfaces, such as bone.

Accordingly, there is a need for improved surgical devices and methods that can address these and other shortcomings of prior solutions for drilling into bone or other hard tissue with precision.

SUMMARY

Systems, methods, and devices are disclosed for surgical instruments, systems, and methods for preventing skiving of a surgical instrument, such as an instrument used during a robotic or robot-assisted surgery.

A surgical system is described herein, comprising a robot arm configured to position a tool for receiving one or more drilling instruments relative to patient anatomy, and a controller coupled to the robot arm and configured to: receive a target trajectory for drilling a hard tissue, the target trajectory having a target entry point, a target diameter, a target axis, and a target depth; analyze a three-dimensional model of the hard tissue, including a surface curvature of the hard tissue at the target entry point; determine that a skiving threshold is surpassed, wherein surpassing the skiving threshold indicates skiving is at least likely while drilling along the target orientation; and determine an anti-skiving trajectory for drilling the hard tissue before drilling the target trajectory, wherein the anti-skiving trajectory differs from the target trajectory by at least one of entry point, diameter, axis, or depth.

A robot instrument positioner for a surgical tool is described herein, comprising a coupler for connecting the robot instrument positioner to a robot arm of a surgical system, a guide rail for engaging the tool, and a first pivot assembly and a second pivot assembly attached to the guide rail for varying a longitudinal axis of the tool in response to a command from a controller.

A surgical method is described herein, comprising receiving a target trajectory for drilling a hard tissue having a target entry point, a target orientation and a target depth, analyzing a three-dimensional model of the hard tissue using a digital data processor to determine that a surface curvature of the hard tissue at the target entry point surpasses a skiving threshold that indicates skiving is likely while drilling along the target orientation, calculating an anti-skiving trajectory using the digital data processor, the anti-skiving trajectory having an anti-skiving orientation and an anti-skiving depth that are different from the target orientation and the target depth such that the anti-skiving trajectory alters the curvature of the hard tissue at the target entry point to be below the skiving threshold while drilling along the target orientation.

DETAILED DESCRIPTION

Figure 1:
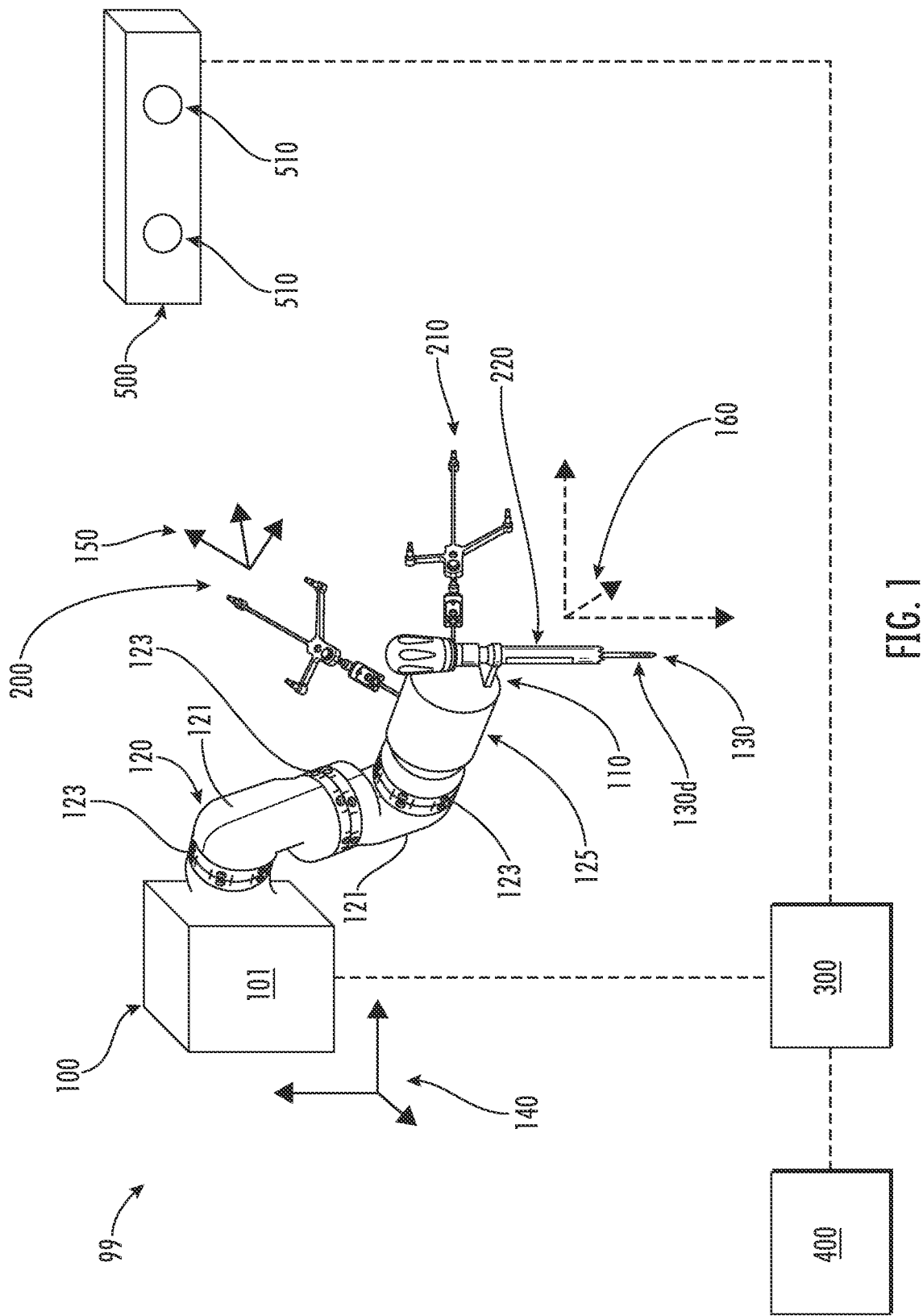
FIG. 1 is a schematic diagram of a surgical system including a surgical robotic device with an attached end effector for orienting a tool having a cutting instrument along a trajectory for reducing, preventing, and/or correcting skiving according to the present disclosure.

Drilling and/or other cutting of bone should be planned carefully. Such surgical pre-planning can include a target trajectory for drilling a hole including target entry point, orientation, speed, diameter, and depth. However, spinal geometry is variable and often not flat at the optimal entry point (e.g., a pedicle surface) for a drill tip on the target trajectory. When a pointed cylindrical drill tip contacts a curved surface (or a flat surface at such an angle that relative curvature is created between the components), the drill tip can have a tendency to move off target trajectory as drilling is initiated (e.g., skiving). Skiving results in a hole trajectory through the bone that is different than the planned target trajectory, and can produce undesirable results, such as pedicle breach or compromised screw purchase.

The present disclosure provides surgical instruments, systems, and methods for preventing skiving of a tissue removal (e.g., cutting, drilling, etc.) instrument during a robotic or robot-assisted surgery. The embodiments disclosed herein can prevent skiving of the instrument in different manners. For example, by use of preoperative planning to determine if skiving is likely and provide one or more of an anti-skive trajectory axis for drilling a starter bore before drilling along a target trajectory axis, utilization of different diameter instruments (e.g., first drilling with a relatively larger anti-skiving instrument to create a flat for the relatively smaller target instrument to engage, or first drilling with a relatively smaller anti-skiving instrument to create the starter bore (e.g., hole) for the relatively larger trajectory instrument to engage), and a high-speed compensation feature by utilizing the greater precision and accuracy of a robot instrument positioner that can be coupled to a robot arm and utilized to control a tool having a tissue removal instrument, the robot instrument positioner being configured to counter skiving during, for example, a drilling operation. Additional details on example embodiments are found below.

The following description and figures illustrate embodiments of robot-assisted surgical systems that can be utilized with the systems and methods described herein to prevent, reduce, or correct skiving of a surgical tool. Such systems can utilize any of surgical navigation/tracking and robot control or assistance to monitor or control movement of one or more surgical instruments during a procedure. While the illustrated embodiments and accompanying description can make reference to a specific surgery, the systems and methods described herein can be utilized in various applications involving robotic, robot-assisted, and non-robotic operations where computer-assisted tool location are desired and precise adjustment of tool position can be appropriate. Example applications include knee surgery, such as total knee arthroplasty (TKA), spinal fusion surgery, and other orthopedic surgeries. The teachings of the present disclosure can be applied to such procedures, however, the systems and methods described herein are not limited to these applications.

FIG. 1 shows an overview of one embodiment of a surgical system 99 according to the present disclosure. A robotic device 100 comprises a base 101. The robotic device 100 includes an attached tool end effector 110 and a robot arm 120 having a plurality of arm segments 121 connected by rotatable joints 123. A distal segment 125 of the robot arm 120 includes a navigation array 200 mounted thereto and terminates at distal end with the tool end effector 110. The tool end effector 110 retains (e.g., indirectly or directly) a tool 130, which can have a cutting instrument at a distal tip 130d. The cutting instrument can be, or example, a drill, saw blade, burr, reamer, mill, knife, or any other implement that could cut or deform bone or other tissue and is appropriate for use in a given operation (e.g., a planar saw can be more appropriate in one operation while a rotary burr can be more appropriate in another operation, etc.).

The system can have a plurality of positioning systems, such as a global coordinate system 140 of the robotic device 100 and an end effector coordinate system 160 of the tool end effector. The global coordinate system 140 can be defined in different ways, but generally uses the location of the base 101 of the robotic device 100, which might not itself be stationary. The location of the distal segment 125 can be calculated by receiving a position signal from an encoder in each joint 123. Additionally, a position of the navigation array 200 can be measured in order to directly detect the position of the distal segment 125 and determine the position of the distal end thereof in the global coordinate system 140. In some instances, a measured coordinate system 150 of the navigation array 200 can be used as the global coordinate system 140. The end effector coordinate system 160 can be defined in different ways, but can refer to the position and orientation of the tool end effector 110 with respect to the operation of the tool end effector (e.g., if the tool end effector includes a cutting bit, the cutting direction can be along an "up" or "down" axis).

The tool end effector 110 held by the robotic device 100 is constrained to move about the distal end of the distal segment 125 such that the summation of the positions of the joints 123 defines the location of the end effector coordinate system 160 in the global coordinate system 140. Additionally, or alternatively, the tool end effector 110 can have its own tool navigation system that defines the end effector coordinate system 160. The tool navigation system can include a navigation array 210 and a guide 220. The guide can be an instrument mount or tool holder for the tool 130. In some embodiments, the guide 220 can pivot, as will be described, and can be referred to as a robot instrument positioner, as will be described. The navigation array 210 and the guide 220 can be configured to receive the tool 130 therein, and can identify a position of the tool 130 and the robot arm 120 in absolute space (e.g., can identify or locate a position of the tool 130 and the robot arm 120 with respect to all degrees of freedom of a three-dimension coordinate system, such as the coordinate system 160). Identifying the position of the tool 130 and the robot arm 120 can include identifying a depth position of the tool 130. As used herein, the term "depth" can refer to a position along an axis that runs parallel to a longitudinal axis of the tool 130 and/or the guide 220. The mounted array 210 can identify a depth positioning of the tool 130 received within the instrument guide 220. In this manner, the navigation array 210 can help provide complete positioning information to a control unit of surgical robot system (as will be described) and/or a user (e.g., a surgeon, nurses, practitioners, etc.) by identifying an absolute position of the robot arm 120 and the tool 130, as well as a depth position of the tool tip 130d associated therewith.

The robotic device 100 can be coupled with a control unit or controller 300 that controls the actuation of each joint 123 in order to position the tool end effector 110 (and thus the tool 130). The controller 300 typically includes a power supply, AC/DC converters, motion controllers to power the motors of the actuation units in each joint 123, fuses, real-time interface circuits, and other components conventionally included in surgical robotic devices. Further features of the controller 300 will be described with reference to FIG. 3.

An external device 400 can communicate with the controller 300. The device 400 can be a display, a computing device, remote server, etc., configured to allow a surgeon or other user to input data directly into the controller 300. Such data can include patient information and/or surgical procedure information. The device 400 can display information from the controller, such as alerts. Communication between the device 400 and the controller 300 can be wireless (e.g., near-field communication (NFC), WIFI™, BLUETOOTH™, BLUETOOTH LE™, ZIGBEE™, and the like) or wired (e.g., USB or Ethernet).

The system also includes a navigation system tracking unit 500, such that the relative pose or three-dimensional position and orientation of the navigation array 200 and/or 210, as well as any other navigation arrays present in an operating theater, e.g., such as an array coupled to patient anatomy, a surgical table, etc., can be tracked in real time and shared to the controller 300 and any additional planning system. In some instances, coordinate systems can be attached to the robotic device 100 via the navigation array 200, the end effector 110 via the tool array 210, and an anatomical structure (e.g., an array coupled with patient anatomy). The tracking unit 500 can measure the relative motions between any and all coordinate systems in real time. Real time can, in some embodiments, mean high frequencies greater than twenty Hertz, in some embodiments in the range of one hundred to five hundred Hertz, with low latency, in some embodiments less than five milliseconds.

Figure 2:
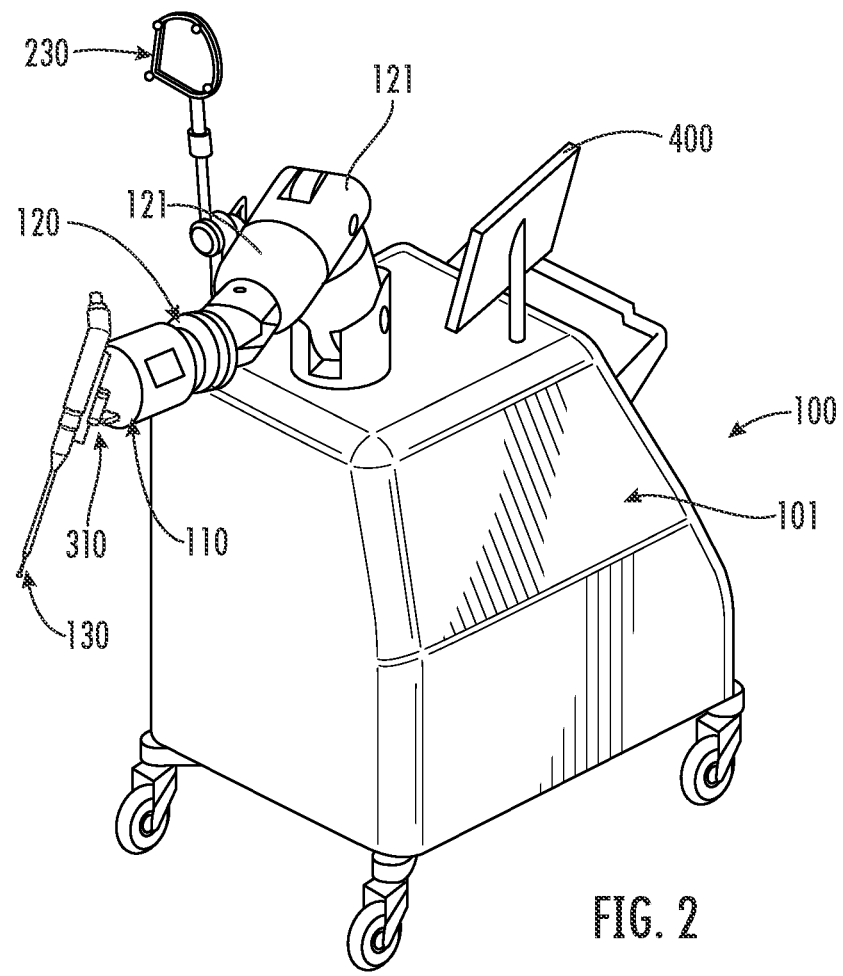
FIG. 2 is a schematic diagram of another embodiment of a robotic device.

In some embodiments, the tracking unit 500 can include one or more navigation system camera(s) 510 that can capture a location of the one or more markers in the arrays 200, 210, and/or 230 (FIG. 2). To that end, the tool array 210 can include one or more markers. A navigation system camera 510 can capture a location of the one or more markers. The array 210 can be coupled with a known and precise relationship to the tool 130. In some embodiments, an array can be coupled to the guide 220 which, in turn, can be coupled to the distal end of the robot arm 120. The array 210 can be coupled to the distal end of the robot arm 120 such that relative movement between the main array and the distal end of the robot arm 120 is restricted. In other words, an array can be stationary relative to a component to be tracked, such as the distal end of the robot arm 120. The location information captured from the markers of an array can thus identify a location of the component to which it is coupled in three-dimensional space given the known and precise relationship between the array and the component.

The array 210 can be configured to locate the depth of the distal tip 130d of the tool 130 when the tool is received within the instrument guide 220. The array 210 can be configured to identify the depth position of the tool 130 without being permanently connected or fastened to the tool 130. As described in more detail below, for example, the tool 130 can pass through a lumen of the array 210 and can drag or move the array 210 distally with distal translation of the instrument. The array 210 and its markers can move linearly with translation of the tool 130. Accordingly, a position and/or movement of the array 210, as captured by the navigation system camera 510 viewing the markers of the array 210, can identify and track the depth position of the tool 130.

In a manner similar to the arrays discussed above, a further array (not shown) can be coupled with a patient or other structure in the operating environment (e.g., a surgical table, etc.), to assist with keeping tracking of an anatomy of interest, for example, a pedicle of the spine and, in some embodiments, providing information to the controller 300. A patient coordinate system can be defined in different ways (e.g., using an array coupled to the patient), but can refer to the position and orientation of the patient with respect to the end effector 110 or tool 130. The tracking system 500 can track these objects for purposes of displaying their relative positions and orientations to the surgeon, for example, using the display 400, and, in some cases, for purposes of controlling and/or constraining manual manipulation of the tool 130 relative to virtual boundaries associated with the patient's anatomy, for example, using the controller 300. Alternatively, information about a patient (e.g., patient anatomy) can be determined through scans (e.g., X-Ray, CT, MRI or ultrasound, etc.) such by an imaging device and provided to the controller 300.

FIG. 2 illustrates another embodiment of a surgical robotic device 100' for use in a surgical system, such as the surgical system of FIG. 1. The robotic device 100' can include a robot arm 120 having multiple arm segments 121 joined together by a plurality of joints. The robot arm 120 can be coupled to a movable cart at its base 101. Additionally, one or more navigation arrays 230 can be coupled to various parts of the robotic device 100, but it is understood a plurality of arrays (200, 210) and a navigation system tracking unit 500 as discussed above in connection with FIG. 1 can be employed. Additionally, the robot arm end effector 110 is attached to a robot instrument positioner 310 (e.g., to retain the tool 130). The robot instrument positioner 310 can be configured to hold and control a position and/or orientation and/or operation of a tool 130 or other surgical instrument, e.g., in response to commands from the controller 300. For example, the robot instrument positioner 310 can pivot with respect to the end effector 110, giving the system even more maneuverability and finer adjustment possibilities than that afforded by the robot arm 120.

Figure 3:
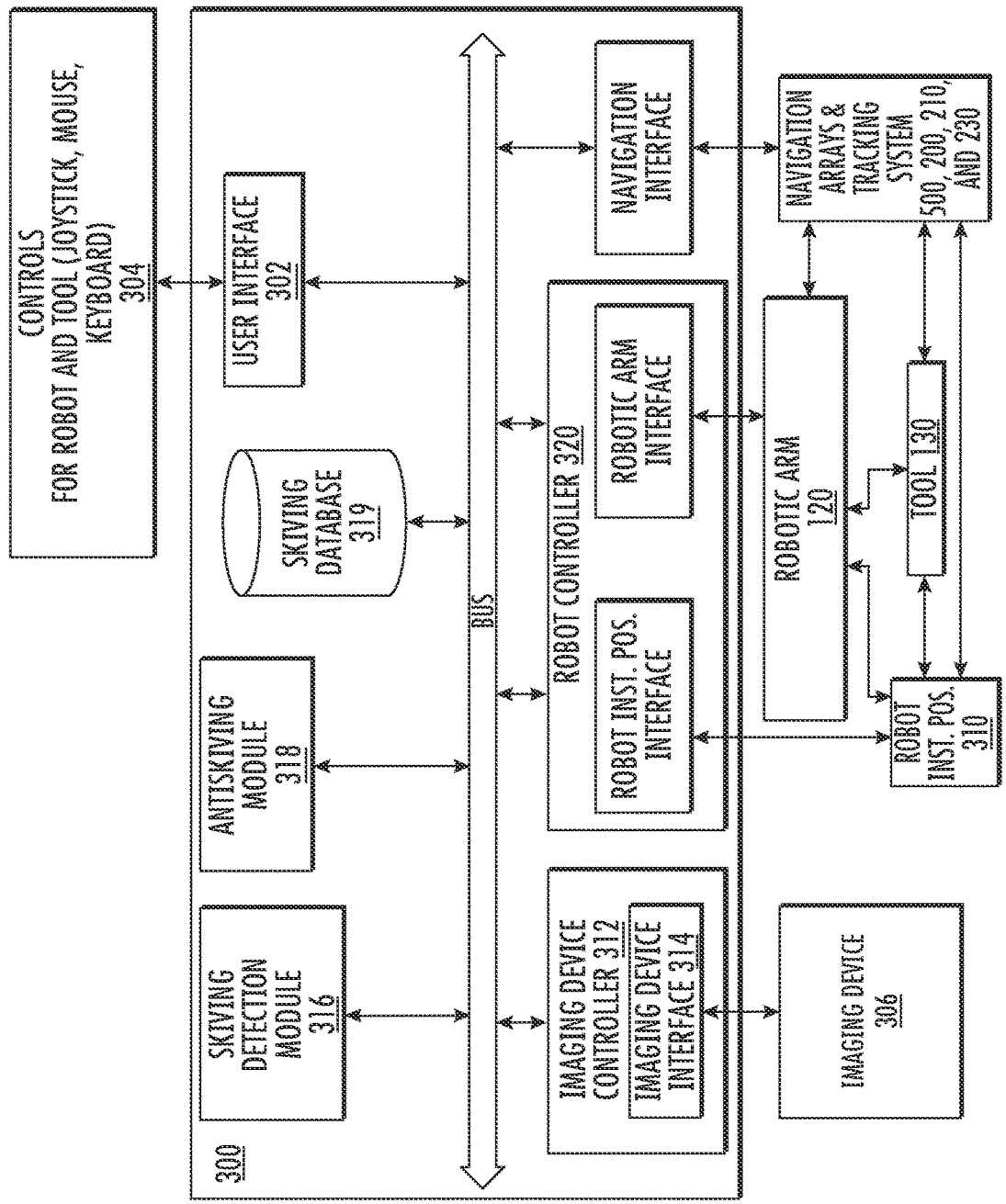
FIG. 3 illustrates functionality of the controller of the surgical system.

FIG. 3 is a schematic diagram of the controller 300, which can be configured for reducing, preventing, and/or correcting skiving. The controller 300 can assist in performing a surgery by accurately tracking movement of one or more surgical instruments and/or assisting or controlling movement of one or more surgical instruments in at least one degree of freedom. In some procedures, the controller 300 controls (via a robotic device (e.g., 100 or 100') positioning of a cutting instrument (such as part of a tool 130) or constrains a surgeon's movement of the instrument in one or more degrees of freedom and allows drilling to be performed independently.

The controller 300 can have a user interface 302 configured to receive input commands from an external control 304. The external control 304 can include a direct wired connection, or a wireless connection, with a keyboard, a foot switch, a mouse, a joystick, and/or other robot and tool controls. Through the user interface 302, a user (for example a surgeon) can control various other devices, such as a PACS system to (not depicted) store or retrieve patient data, an imaging device 306, a navigation tracking system 500, a robot arm 120, one or more navigational arrays 200, 210, a robot instrument positioner 310, and/or a tool 130 coupled therewith. Furthermore, the surgeon can input parameters regarding a target trajectory through the user interface 302. The target trajectory can include a target entry location, target orientation, target speed, target diameter, and target depth, among other parameters.

An imaging device controller 312 can be configured to control the imaging device 306 and/or scanner (referred to as imaging device 306 for convenience), such as an X-ray, ultrasound, MRI, coordinate measuring-machine, camera, etc. To that end, the imaging device controller 312 can have an imaging device interface 314 configured to communicate with the imaging device 306. The imaging device 306 can be configured to image or scan a portion of patient anatomy through which a hole is to be drilled. Specifically, the imaging device 306 can scan at least a portion of the surface to be drilled, including the target entry location based on the target trajectory. Curvature of anatomy, bone hardness, and other properties can be determined. A user interface for planning and/or navigation can be used to plan a target trajectory.

The imaging device controller 312 can communicate with a skiving detection module 316. The skiving detection module 316 can receive the results of the scan, including the target entry location, and determine whether a shape and/or curvature of the bone at the entry location is likely to cause skiving (e.g., if the tissue removal (e.g., drilling, cutting, etc.) instrument can penetrate the surface without skiving). To that end, the skiving detection module 316 can analyze scan results using auto-segmentation to identify the surface relative to other anatomy, and determine whether there are irregularities and/or sufficient curvature of the surface to cause skiving. In some embodiments, skiving detection module 316 can determine that skiving is likely even if the surface is relatively flat, e.g., based on an angle of incidence between the instrument and the surface based on the target trajectory, or by evaluating bone hardness (such as by determining HU values of the CT scan). For example, the target trajectory can dictate that the instrument and surface to be drilled will meet at a trajectory similar to drilling into a surface with greater curvature. In some embodiments, the skiving detection module 316 can include machine-learning protocols, with access to a skiving database 319 containing results of prior scans and skiving outcomes (e.g., to be used as a training set). The skiving detection module 316 can thus be trained on prior datasets to determine the likelihood that skiving will occur at the selected location, depth, diameter, speed, and orientation.

An anti-skiving module 318 can calculate an anti-skiving trajectory. The anti-skiving trajectory can be configured to create a small drill point or bore on the bone in the vicinity of the target entry point (and in some instances, at the target entry point), but from a different angle where the drill contacts a less curved surface or the angle between the surface and drill is closer to perpendicular. Accordingly, in some embodiments, it is understood that the anti-skive trajectory is not the same as the target trajectory (e.g., based on parameters input by the surgeon). Generally speaking, the drill point or bore can be shallow, on the order of a millimeter or less. In some embodiments, however, the anti-skiving trajectory can have a depth of a centimeter or less. In another embodiment, the anti-skiving module 318 can determine a utilization of a pair of geometrically different tissue removal instruments (e.g., first drilling with a relatively larger instrument to create a flat for the relatively smaller instrument to engage, or alternatively, first drilling with a rounded instrument followed buy a pointed instrument). In this embodiment, the anti-skive trajectory could be the same as the target trajectory in some instances. In another embodiment, the anti-skiving module 318 can determine to employ a high-speed compensation feature by utilizing the greater precision and accuracy of the robot instrument positioner (e.g., that can be coupled to the robot arm and utilized to control the tool 130) to counter skiving as detected. In some embodiments, the anti-skiving module 318 and skiving detection module 316 can form a generative adversarial neural network. For example, the anti-skiving module 318 can be a generative neural network configured to generate candidate anti-skiving trajectories configured to change the shape of the surface of the bone at or near a target entry point. The skiving detection module 316 can operate as a discriminative neural network configured to receive the one or more candidate anti-skiving trajectories from the anti-skiving module 318, and to determine whether the one or more anti-skiving trajectories modify the surface of the bone such that the surface no longer passes the skiving threshold. This process can be an iterative process.

A robot controller 320 can be configured to control a robotic device (e.g., such as the robotic device 100 of FIG. 1 or the robotic device 100' of FIG. 2). To that end, the robot controller 320 can have an interface configured to communicate with the robotic device and move one or more of a robot arm, an end effector, and a robot instrument positioner, to control a tool (such as the tool 130). The robot instrument positioner 310 can be coupled to the distal end of the robot arm 120, for example. The robot controller 320 can control the position of a tool 130 directly or indirectly, by controlling a position of the robot arm 120, the end effector 110, the guide 220, and/or the robot instrument positioner 310. To that end, the robot controller 320 can communicate with the navigation tracking system 500. Furthermore, in some embodiments, the tool 130 can be controlled manually by the surgeon, or can be controlled at least partially manually with at least partial robotic control (e.g., force assist from a robot or robotic constraint against movement beyond certain bounds or in certain planes while otherwise providing for manual control, limiting speed depending on position relative to the bone, determining to keep on a straight line or pivot around the instrument tip).

Figure 4:
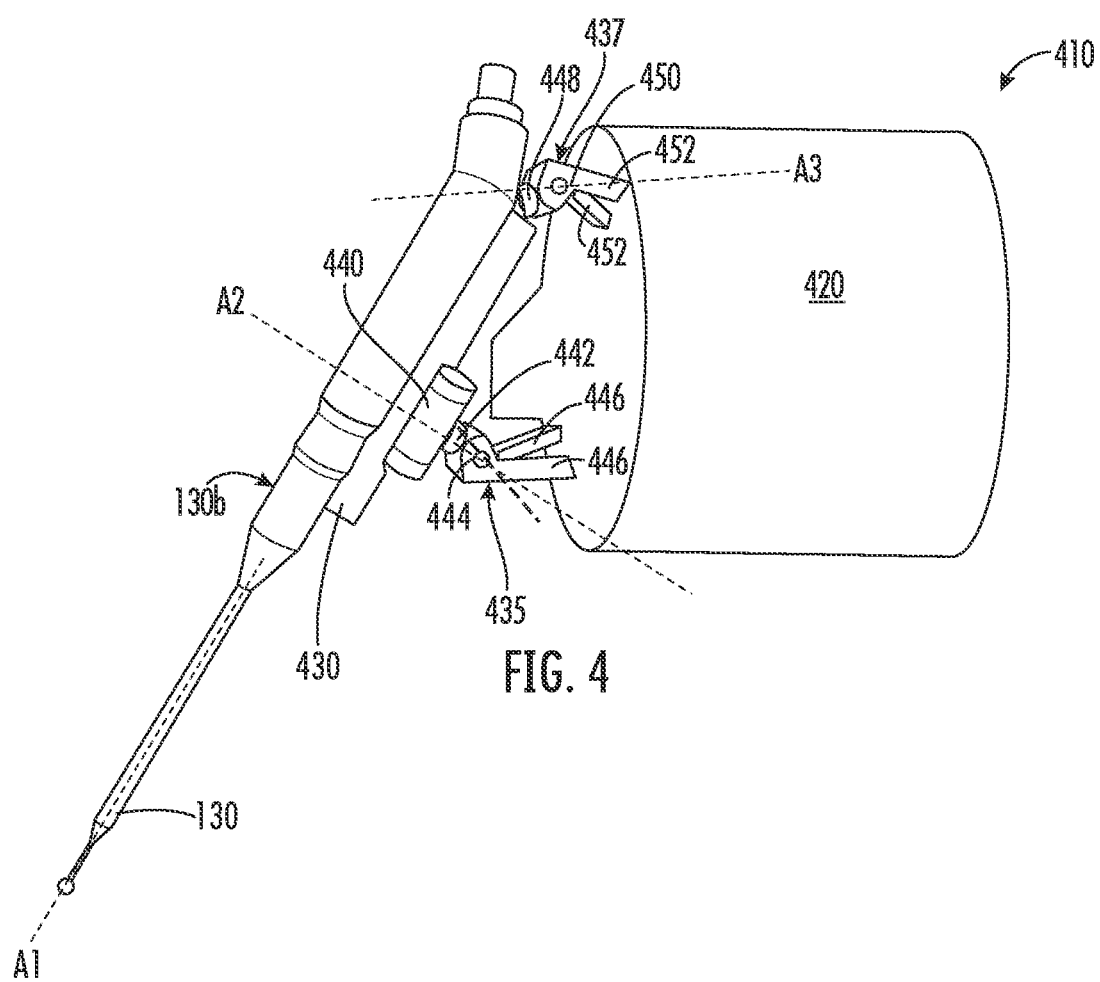
FIG. 4 illustrates a robot instrument positioner and tool for use in the surgical system.

FIG. 4 illustrates a robot instrument positioner 410, which has a body 420 which can be attached to a robot arm (e.g., either directly or via an end effector). The robot instrument positioner 410 can provide faster and more precise movements than can be achieved using the robot arm alone. A tool 130, such as a tool having a rotary burr, can be coupled to the robot instrument positioner 410.

For example, a tool body 130b can be attached to a guide rail 430 of the robot instrument positioner 410. As can be appreciated, a longitudinal axis A1 is defined by an axis of the tool 130. In some embodiments, the tool 130 can be translated relative to the guide rail 430 to control axial advancement or retraction (e.g., along longitudinal axis A1). The robot instrument positioner 410 can be configured to selectively lock the guide rail 430 and tool 130 against movement once properly positioned. The guide rail 430 is slidably disposed upon a first pivot assembly 435 and a second pivot assembly 437. The first pivot assembly 435 has a carriage 440, a support 442, a pivot point 444, and a connector 446. As can be appreciated, a first radial axis A2 is defined by an axis of the pivot point 444. The second pivot assembly 437 has a carriage (not visible), a support 448, a pivot point 450, and a connector 452. As can be appreciated, a second radial axis A3 is defined by an axis of the pivot point 450. The robot instrument positioner 410 further comprises actuators (not visible) to move a trajectory of the tool body 130b (e.g., upon a command by the controller (FIG. 3)) by pivoting on one or more of the first pivot assembly 435 and the second pivot assembly 437. Such pivoting, in addition to the axial movement along the guide rail 430, allows for three degrees of freedom for the tool 130. Further, and as explained in more detail below, the robot instrument positioner 410 can be configured to provide more accurate, precise, and rapid detection of movements of the tool 130, as well as more accurate, precise, and rapid adjustments of the tool instrument positioning than is possible using the robot arm (e.g., alone) and, in some cases, than can be detected using a navigation array-based tracking system as described herein. In some embodiments, the robot instrument positioner 410 can be equipped with force or deflection sensors disposed throughout the robot instrument positioner, such as in connection with actuators that control movement of the drilling instrument.

Figure 5:
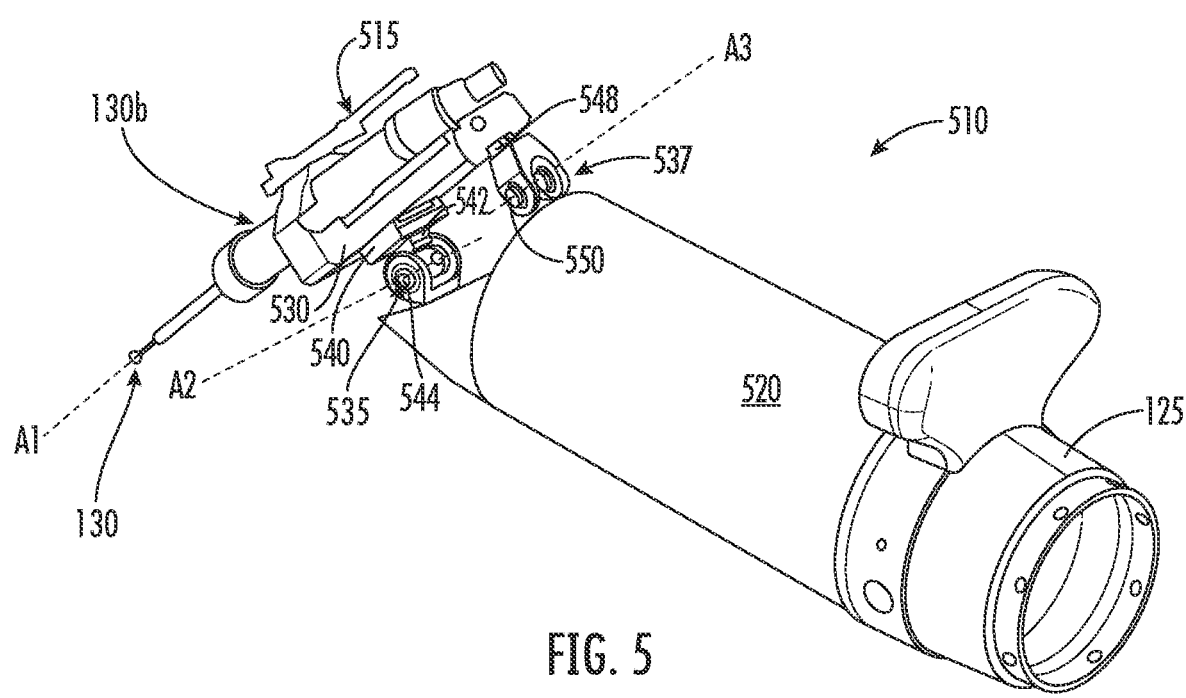
FIG. 5 illustrates another embodiment of a robot instrument positioner and tool for use in the surgical system.

FIG. 5 illustrates another embodiment of a robot instrument positioner 510 with a quick change mechanism 515 allowing for rapid swapping of tools 130 and tool sizes. The robot instrument positioner 510 is coupled to a distal segment 125 of a robot arm, such as at a body 520. A tool body 130b can be attached to a guide rail 530 of the robot instrument positioner 510. As can be appreciated, a longitudinal axis A1 is defined by an axis of the tool 130. In some embodiments, the tool 130 can be translated relative to the guide rail 530 to control axial advancement or retraction (e.g., along longitudinal axis A1). The robot instrument positioner 510 can be configured to selectively lock the guide rail 530 and tool 130 against movement once properly positioned, e.g., via quick change mechanism 515. The guide rail 530 is slidably disposed upon a first pivot assembly 535 and a second pivot assembly 537 connected to the body 520 of robot instrument positioner 510. The first pivot assembly 535 has a carriage 540, a support 542, and a pivot point 544. As can be appreciated, a first radial axis A2 is defined by an axis of the pivot point 544. The second pivot assembly 537 has had a portion removed for simplicity of illustration, but is understood to be connected to the body 520 to achieve a pivot. The second pivot assembly 537 includes a carriage (not visible), a support 548, and a pivot point 550. As can be appreciated, a second radial axis A3 is defined by an axis of the pivot point 550. The robot instrument positioner 510 further comprises actuators (not visible) to move a trajectory of the tool body 130b (e.g., upon a command by the controller (FIG. 3)) by pivoting on one or more of the first pivot assembly 535 and the second pivot assembly 537. Such pivoting, in addition to the axial movement along the guide rail 530, allows for three degrees of freedom for the tool 130. Further, and as explained in more detail below, the robot instrument positioner 510 can be configured to provide more accurate, precise, and rapid detection of movements of the tool 130, as well as more accurate, precise, and rapid adjustments of instrument positioning than is possible using the robot arm (e.g., alone), and, in some cases, than can be detected using a navigation array-based tracking system as described herein. For example, in some embodiments, the robot instrument positioner 510 can be equipped with force or deflection sensors disposed throughout the robot instrument positioner, such as in connection with actuators that control movement of the drilling instrument.

Figure 6:
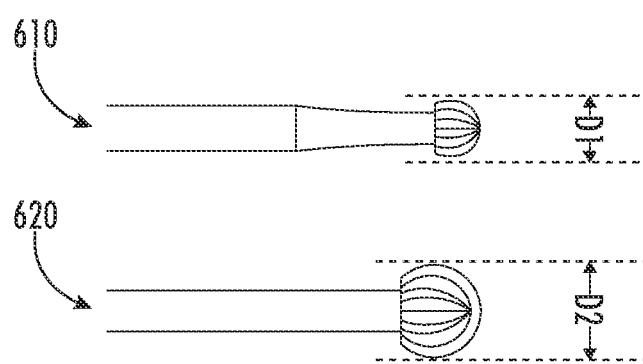
FIG. 6 illustrates drilling instruments of differing diameters.

FIG. 6 illustrates two different rotary burr drilling instruments that can be used (e.g., selected by the anti-skiving module of the controller) in some embodiments as part of the tool 130. In some embodiments, an initial trajectory can be determined to use a small diameter tool, such as burr 610, which has a diameter D1. The burr 610 has a relatively smaller diameter than burr 620, which has a diameter D2. The burrs 610 and 620 can be used successively, e.g., first drilling with a relatively larger anti-skiving instrument to create a flat for the relatively smaller target instrument to engage, or first drilling with a relatively smaller anti-skiving instrument to create the starter bore (e.g., hole) for the relatively larger trajectory instrument to engage. In some embodiments, the smaller diameter burr 610 can be coupled with a robot instrument positioner (such as those of FIGS. 4&5), which can be associated with a high-speed compensation system of the controller (FIG. 3). The high-speed compensation system can reduce the risk of skiving and/or be able to quickly correct skiving before too much bone is removed at a misaligned trajectory relative to the target trajectory. The shape of the cutting surfaces on the burrs 610 and 620 can result in them being less likely to skive on a curved surface (e.g., as compared to a pointed cylindrical drill). This can be because the cutting surface immediately contacts the bone and starts to remove material. Additionally, if the burr 610 (or burr 620) is coupled to the robot instrument positioner that is monitoring the trajectory, the controller can sense the burr moving off trajectory and provide an adjustment (along at least one radial axis) to correct the trajectory quickly (e.g., nearly instantaneously). In another embodiment, the controller (e.g., the anti-skiving module) can determine a utilization of a pair of different diameter tissue removal instruments, for example, first drilling with a relatively larger instrument such as burr 620 to create a flat for a relatively smaller instrument (such as burr 610 or a pointed cylindrical drill (not depicted)).

Figure 7A:
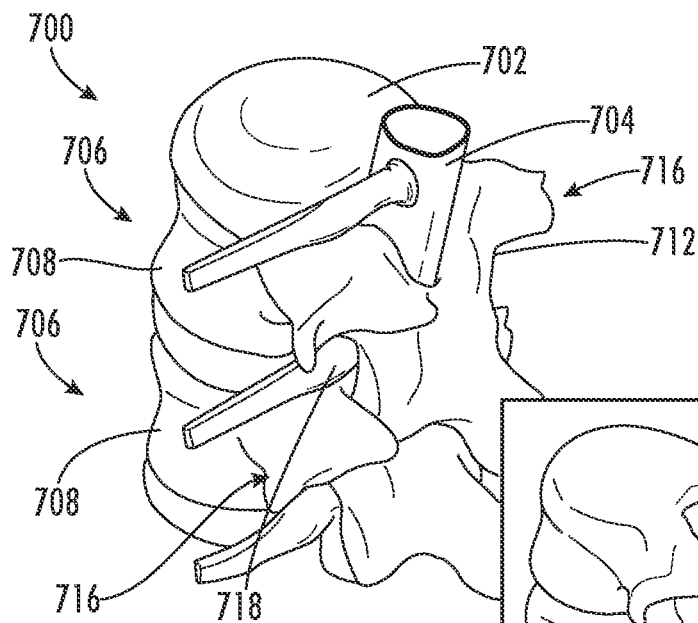
FIGS. 7A-7D are illustrations of example patient anatomy.
Figure 7B:
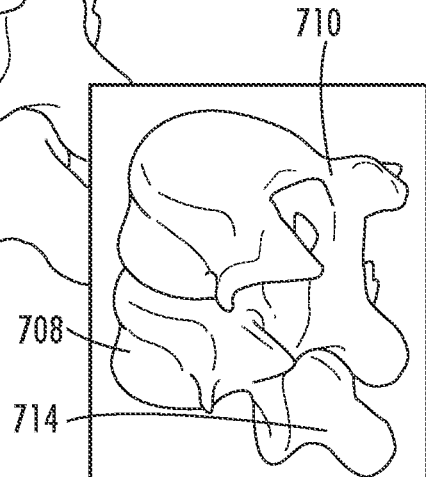

In some embodiments, surgical systems, methods, and instrumentalities of the disclosure will find use in spinal-related procedures. FIGS. 7A-7D are illustrations of a patient's spinal column 700. Specifically, FIG. 7A shows a rear perspective view of the spinal column 700 having discs 702 and a spinal cord 704. FIG. 7B shows the same view without the discs 702 and the spinal cord 704. The spinal column 700 has a plurality of hard tissue (e.g., bone) vertebrae 706. Each vertebrae 706 has a body 708 and a vertebral arch formed by two pedicles 710 extending posteriorly from the main body and leading to two laminae 712 that terminate medially at a spinous process 714 and laterally at two transverse processes 716. A foramina 718 is adjacent the transverse process 716.

Figure 7C:
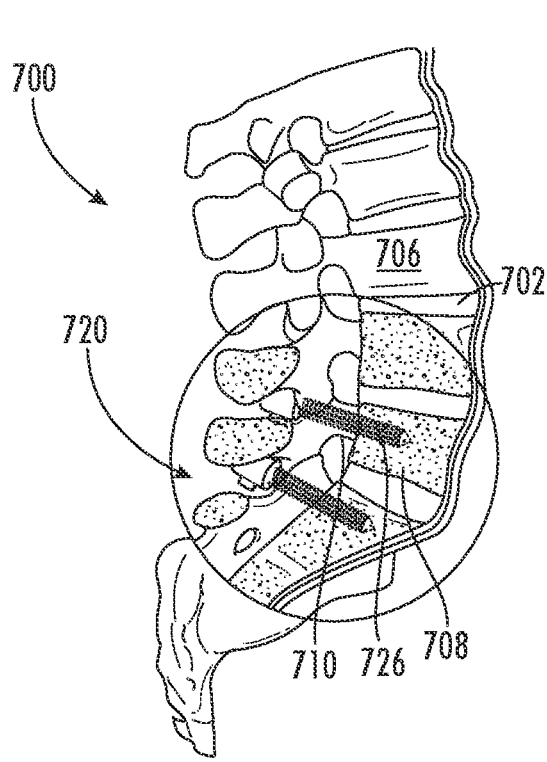
Figure 7D:
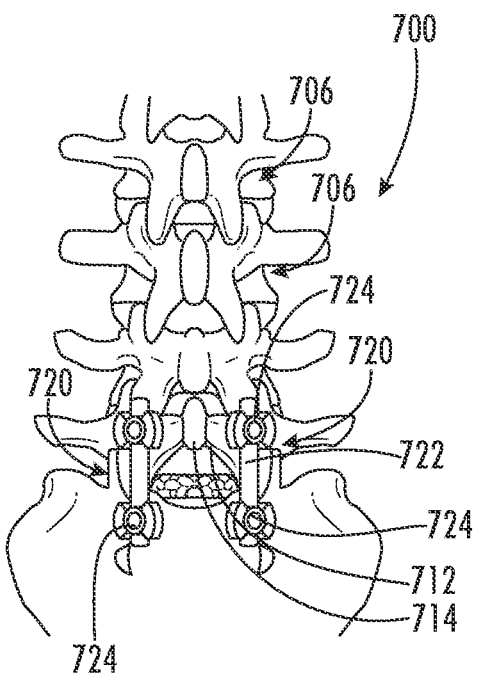

FIGS. 7C and 7D show a side view and a rear view, respectively, of the spinal column 700 during a surgical procedure such as a spinal fusion. Specifically, the surgical procedure shows a pedicle screw-rod system 720 including a rod 722 coupled with rod connectors 724 and a bone anchor or screw 726. Due to the intricacies of working in proximity to the spinal column 700, spinal surgery procedures can require great precision and accuracy to avoid undesirable outcomes. For example, such procedures typically require spinal fixation assemblies to be delivered directly (e.g., substantially perpendicular to the midline of the patient's spinal column) into a lateral mass or pedicle 710 of a target vertebra. In light of this trajectory, slight deviations from a desired delivery trajectory can result in penetration of a distal portion of the assembly (e.g., a pointed tip of a bone screw shank) into the spinal canal (which contains the spinal cord) or the foramina of the exiting nerve root, which can be undesirable. As a further disadvantage, the limited bone mass and/or bone density that can be found in the lateral mass portion of a vertebra can limit the area available for contacting the pedicle screw-rod system 720, thereby hindering the ability to effectively position the pedicle screw-rod system within the vertebra.

Figure 8:
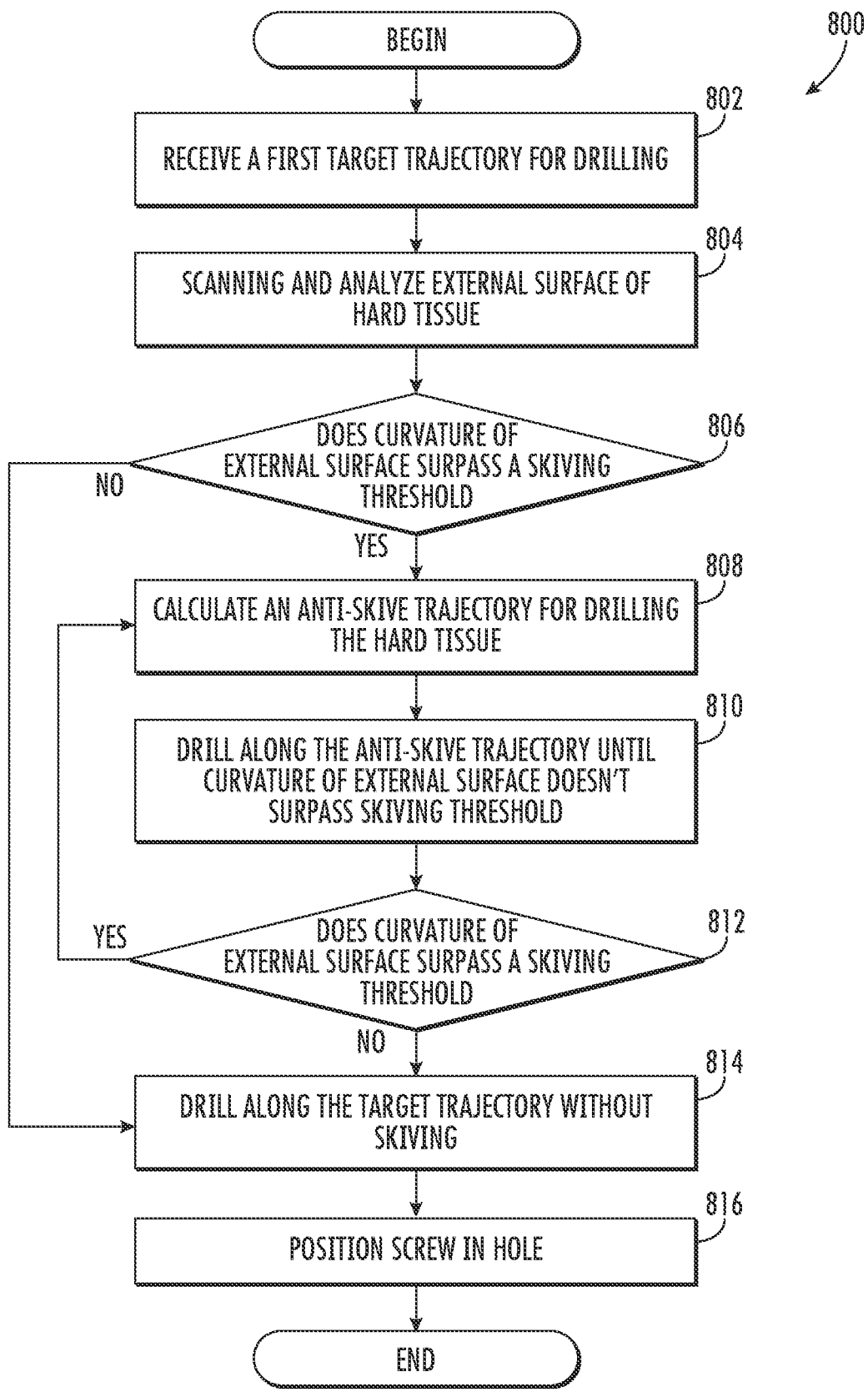
FIG. 8 is a flowchart of a method of reducing and/or preventing skiving.

FIG. 8 is a flowchart of one embodiment of a method 800 of reducing and/or preventing skiving. It should be noted that discussion of this process is illustrative and not intended to limit various embodiments of the invention (e.g., portions of the flowchart are referred to as steps, but it is understood that the steps can be omitted, repeated, sub-divided, concurrently performed, or performed in a different order without departing from the spirit of the disclosure). In some embodiments, the method is performed using the above-described surgical system (e.g., FIG. 1 et. seq.).

At step 802, a first target trajectory for drilling is received. The target trajectory can be stored in memory or can be inputted (e.g., to the controller 300 (FIG. 1 and FIG. 3)) by a user (e.g., surgeon), for example via a user interface. A user can input the diameter and/or length of the hole to be drilled, as well as its position and/or orientation relative to patient anatomy. Alternatively, the user can select a screw model/size, and the properties can auto-populate. As noted, the user can also input the target orientation and position of the screw. Finally, the target trajectory can also be received as an output from another pre-operative surgical planning software utilized to develop a surgical procedure plan. In some embodiments, the system can give feedback on the probability of skiving depending on screw placement and suggest other positions/orientations. One or more of the foregoing can be stored in the controller and used in subsequent determinations.

At step 804, scanning and analysis of the patient anatomy (e.g., an external surface of hard tissue) through which the target trajectory passes can be performed. To that end, the controller (e.g., imaging device controller 312 (FIG. 3)) can automatically control an imaging device (such as imaging device 306 (FIG. 3)) to scan the target entry point, such as by X-Ray, CT, MRI, or ultrasound. This can be accomplished, for example, because the system can know the location of patient anatomy using a surgical navigation system. Alternatively, a technician can manually position the imaging device relative to the patient in a way that captures the target entry point. In some embodiments, scanning and analyzing the external surface of the hard tissue can be accomplished based on an earlier-established pre-operative scan and associated three-dimensional model of patient anatomy created based on the scan data (e.g., using auto-segmentation to identify different components of patient anatomy, etc.). The scan data can be auto-segmented and otherwise analyzed (e.g., by the skiving detection module 316 (FIG. 3) or another system component to create a three-dimensional model of patient anatomy showing the features of the bone or other tissue to be drilled into/through. In some embodiments, a scan and resulting three-dimensional model can be utilized to develop the target trajectory during pre-operative planning and to perform the herein-described anti-skiving analysis and planning.

At step 806, a determination is made (e.g., by the controller) whether the curvature and/or shape of the of the bone at an entry point is such that skiving is likely when drilling along the target trajectory. In some embodiments, this can include determining if the curvature of the surface surpasses a skiving threshold above which skiving is likely and below which it is unlikely. For example, the skiving detection module 316 (FIG. 3) can analyze the scan obtained by the imaging device (or from elsewhere) to determine whether the curvature is likely to cause skiving while drilling. To determine whether the shape of the bone is likely to surpass a skiving threshold, a number of factors can be considered, including a diameter of the hole to be drilled, a curvature at the entry point, an angle of approach, a slope at the entry point, a bone density, a drill tip material, and/or a speed of drill, etc. In some embodiments, the controller (for example, the skiving detection module 316 (FIG. 3) can definitively determine that skiving will or will not occur (e.g., if the skiving threshold is ("YES"), or is not ("NO"), surpassed). Although not depicted, instead of a "YES" or "NO," based on the circumstances, the skiving detection module 316 can output a skiving risk (e.g., high risk, low risk, or a numeric or other representation of risk). This embodiment can be of particular use where the curvature of the surface is within a range that is within 20%, is within 15%, is within 10%, or is within 5%, of the skiving threshold. In some embodiments, the controller can suggest a different trajectory with less skiving probability (so that optimally the screw trajectory and anti skiving trajectory are equal).

If the curvature of the external surface does not surpass a skiving threshold ("NO"), the process can move to step 814, as will be discussed. If the curvature does pass the skiving threshold, however, such that there is a likelihood that skiving will occur, the process can move to step 808.

At step 808, the controller (e.g., the anti-skiving module 318 (FIG. 3)) calculates or determines an anti-skiving trajectory for drilling the bone. A plurality of anti-skiving trajectories can be determined. A determined anti-skiving trajectory can include one or more of an entry point, a depth, an orientation/angle of approach, a speed, and a diameter. In some embodiments, the anti-skiving trajectory can be configured to drill some of the bone at or near the target entry point to make the shape of the bone less likely to cause skiving when drilling from the target trajectory. To that end, the anti-skiving trajectory can approach the target entry point from a different angle (e.g., a different trajectory) than the target trajectory. For example, the anti-skiving trajectory can be oriented such that it is substantially perpendicular to the entry point, or at least more perpendicular than when following the target trajectory. The anti-skiving trajectory can be determined to take advantage of neighboring anatomical features, for example, if the target entry point is near the base of a "valley" of bone, the area immediately around the entry point can be drilled to flatten the area.

The anti-skiving trajectory can specify a preferred tool, e.g., having an instrument (or bit) of a particular size, style, etc., for example, to achieve a calculated diameter. For example, some embodiments can suggest the use of a burr, rather than a pointed cylindrical drill. Additionally, the anti-skiving trajectory can specify the size of the instrument (e.g., burr and/or drill diameter) to optimize the remodeling of the surface at the entry point and/or adjacent areas. In some embodiments, a plurality of instruments (or even a plurality of tools) can be used to remodel the surface of the hard tissue.

At step 810, the anti-skiving trajectory is drilled. In some embodiments, the anti-skiving trajectory can be drilled until the curvature of the external surface does not surpass the skiving threshold and skiving when drilling along the target trajectory is no longer likely. The skiving threshold can be determined as described with respect to step 806, or as will be described with respect to step 812. Regarding the drilling process, the controller can communicate with the navigation system and move the robot arm and/or robot instrument positioner to an appropriate position. A tool can be releasably held by an end effector or robot instrument positioner, allowing use of one or more instruments or other surgical tools. In some embodiments, a surgeon can then manually drill the anti-skiving trajectory after the controller (e.g., robot controller 320 (FIG. 3)) has properly oriented the tool. Alternatively, controller can activate the tool and automate the anti-skiving process.

Operation of the robot arm by the surgeon can permit movement of the tool in a measured, even manner that disregards accidental movements of the surgeon or movements that result in undesirable motion of the tool's instrument. For example, the robot arm can be locked against certain directions of movement. The surgeon and/or controller can move the guide or the robot instrument positioner to achieve proper trajectory of the instrument (e.g., a drill or screw) of the tool prior to operation or insertion of the instrument into the patient. Once the robot arm is in the desired position, the robot arm can be fixed (in one or more degrees of freedom, planes, dimensions, etc.) to maintain a desired trajectory.

Furthermore, the drilling can be fully autonomous (e.g., controller entirely by the controller), manual, or semi-autonomous to allow the surgeon to take over and drill. For example, the robot controller 320 (FIG. 3) can automatically start drilling, or this can be in response to controls 304 (FIG. 3) activated by the user. With a robot arm, not only the trajectory can be controlled, but also the feed forward speed, which can also impact skiving. The instrument (e.g., drill) can then be moved along the anti-skiving trajectory toward the anti-skiving trajectory entry point (which might not be the same as the target trajectory entry point) to form a bore. One or more virtual boundaries (e.g., a virtual fence of a given diameter or axis with a given offset) can be activated to define the anti-skiving trajectory, to keep the drill on the axis of the anti-skiving trajectory, and to prevent the user from drilling outside of the depth and or diameter that is needed for the drill point or bore (e.g., the virtual boundary can be limited in depth). The same virtual boundaries can also be used to provide haptic guidance to the user to initially locate the drill tip on the anti-skiving trajectory axis. Guidance could be done in a hands-on-mode by actively pulling/pushing the surgeon to the target trajectory (like a virtual magnet) or by adding counter forces when the surgeon wants to move to the wrong direction. In both cases the force can be that small that if the surgeon wants, the surgeon can leave the optimal path when applying slightly higher forces. For example, the controller can create a virtual boundary with a diameter the same as or slightly larger than the drill tip, and a depth of the anti-skiving trajectory depth. Thus, any unintended movements that would otherwise cause the drill to move outside of the anti-skiving trajectory can be stopped, with haptic feedback and/or an alarm provided to the user. Forward feed and/or speed can be controlled with haptic guidance as well.

At step 812, the controller scans the hard tissue surface and determines whether the curvature of the external surface surpasses the skiving threshold (e.g., after the anti-skiving trajectory has been drilled). If the surface does surpass the skiving threshold ("YES"), then the process returns to step 808, which calculates a new anti-skiving trajectory (e.g., a second anti-skiving trajectory). This can be done in a manner similar to the process discussed previously. For example, the second anti-skiving trajectory can be drilled to form a different orientation, at a different speed, different entry point, and/or different depth from the first anti-skiving trajectory. The process can then proceed to step 810, which drills the second anti-skiving trajectory. This process can be repeated as many times as necessary to bring the surface below the skiving threshold. After each skiving trajectory is drilled, a new scan of the surface can be taken, for example, by the imaging device.

When the curvature of the external surface does not surpass the skiving threshold ("NO"), such that skiving when following the target trajectory is not likely, the process can move to step 814, which drills along the target trajectory. At step 814, the instrument can be retracted along the anti-skiving trajectory. A different instrument (or a different tool) can be releasably held by an end effector or robot instrument positioner. The robot arm can adjust its position to be optimal for following the target trajectory. The controller can notify the surgeon after achieving optimal positioning. As mentioned previously, drilling can be fully autonomous, semi-autonomous, or manual, as described above. A tip of the drilling instrument can automatically dock into the bore created at step 810 (e.g., so that it cannot skive and instead follows the target trajectory).

At step 816, a screw is positioned in the hole (e.g., the hole drilled in accordance with the target trajectory). Accordingly, the above-described system and method can allow a surgeon to participate to a desired degree in achieving proper alignment of the tool 130 and executing on the desired surgical plan.

Figure 9:
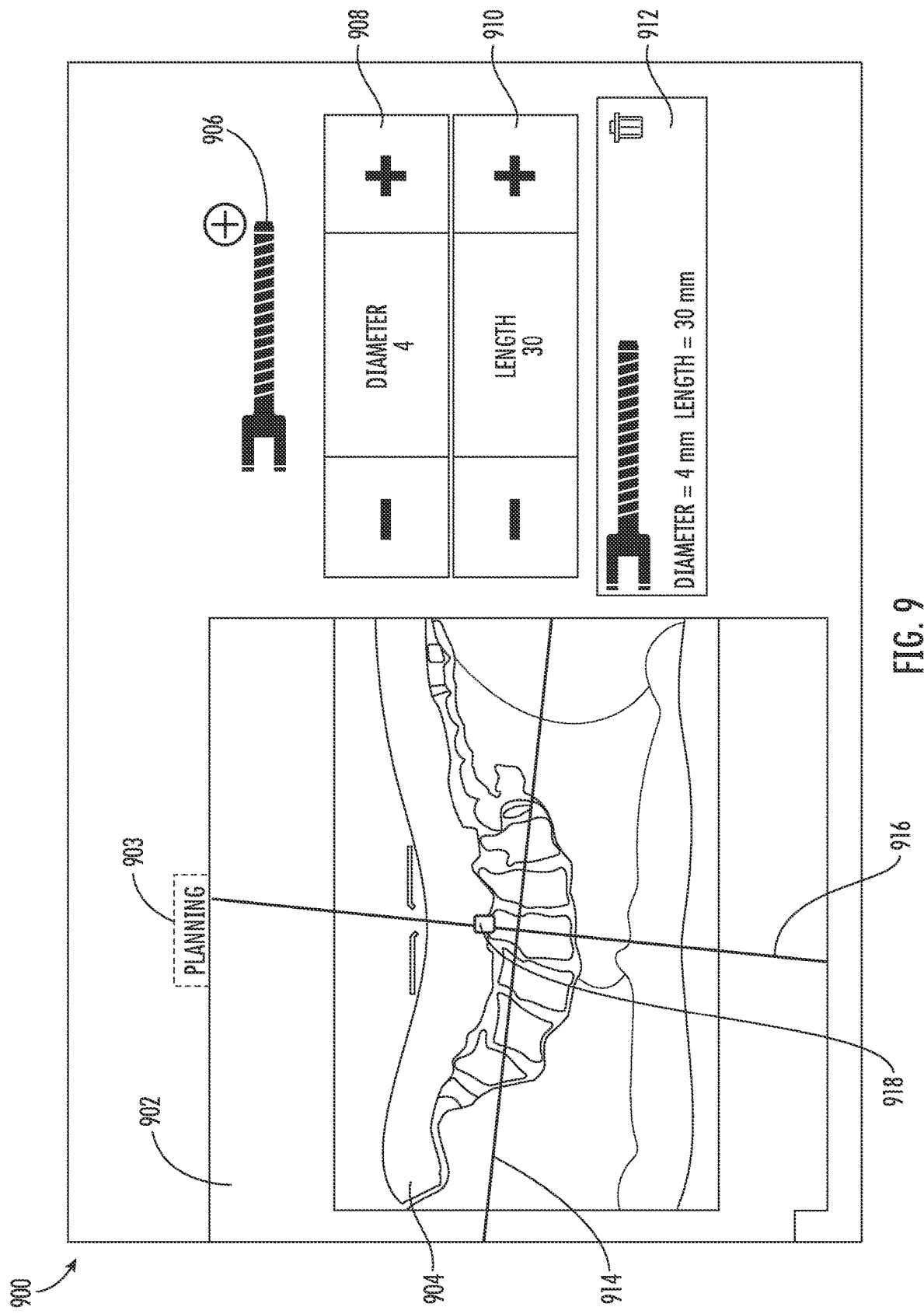
FIG. 9 is a diagram of a user interface for planning a target trajectory using the surgical system.

FIG. 9 is a diagram of a user interface 900 (illustrated as a screenshot) for planning a target trajectory. In some examples, the user interface 900 shares the features of user interface 302 (FIG. 3). The user interface 900 can have an area for displaying images 902 (e.g., such as a scan of the anatomy of the patient, for example, a scan of a hard tissue surface) and/or indicators 903 (e.g., of the stage of a procedure, such as pre-operative surgical planning). A three dimensional model 904 of the patient anatomy can be displayed. Depending on the type of procedure, an indicator 906 of a type of device to be inserted into a hole in the anatomy, such as a screw, can be displayed. A diameter 908 and a length 910, e.g., of the hole, are displayed. A user (e.g., surgeon) can input the diameter and/or length of the hole to be drilled. Alternatively, the user can select a screw model/size, and the properties can auto-populate. A module 912 can be provided to scroll through options, add devices, etc. A target trajectory, e.g., a position and/or orientation of the hole relative to patient anatomy, can be planned, such as by reference to a plurality of axes 914, 916. An entry point 918 can be planned, such as a target trajectory entry point for drilling. The target trajectory can be stored in memory or can be inputted (e.g., to the controller 300 (FIG. 1 and FIG. 3)) by the user. Alternatively, the target trajectory can be received as an output from another pre-operative surgical planning software utilized to develop a surgical procedure plan.

Figure 10:
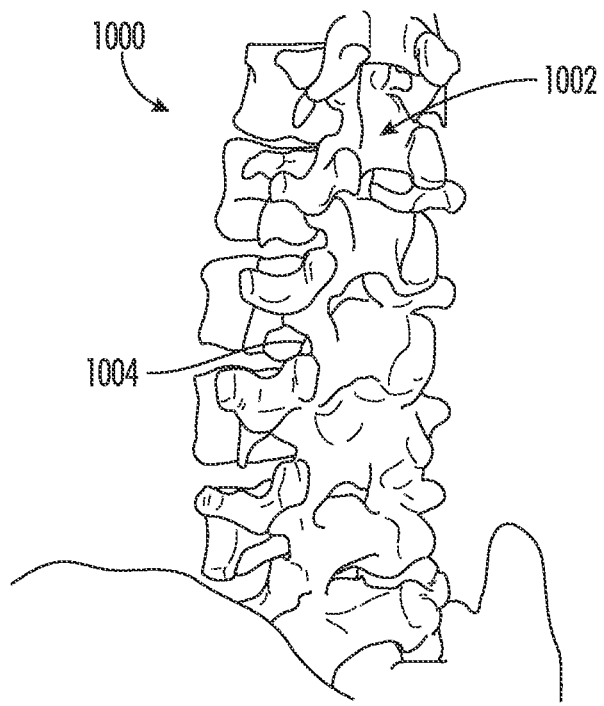
FIG. 10 shows a three-dimensional model of patient anatomy created from a scan of the patient anatomy, including an entry point of a target trajectory.

FIG. 10 shows a scan of the anatomy of the patient 1002 including, optionally, an entry point 1004 (e.g., through which the target trajectory passes) superimposed on the image. The entry point 1004 can, in some embodiments, be moved or repositioned by the user based on the individual anatomy, e.g., to plan the procedure. In some embodiments, the scan can be performed by an X-Ray, CT, MRI or ultrasound, which can image more than the outer surface. In some embodiments, however, computer vision can be used to generate the scan. As noted, the scan data can be auto-segmented and otherwise analyzed by the skiving detection module 316 (FIG. 3) or another system component to create a three-dimensional model of patient anatomy showing the features of the bone or other tissue to be drilled into/through, as will be described with respect to FIG. 11.

Figure 11:
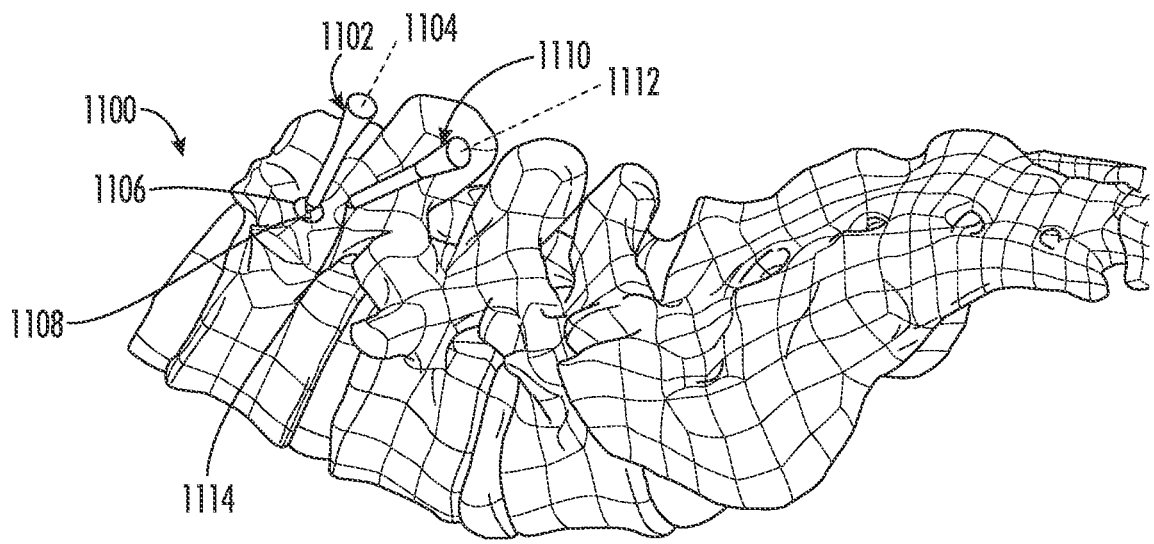
FIG. 11 illustrates a three-dimensional model of patient anatomy, including an entry point of a target trajectory and an anti-skive trajectory.

FIG. 11 illustrates one embodiment of a three-dimensional model 1100 of patient anatomy created from a scan of a patient (such as obtained in FIG. 10). The model 1100 can be displayed on a user interface (such as in FIG. 9). The user can determine a target trajectory 1102. The target trajectory 1102 can comprise one or more of an instrument size, a target trajectory axis 1104, and a target entry point 1106. The target entry point 1104 can be determined to be on a curved area 1108 of hard tissue (e.g., such as bone). The controller 300 (FIG. 3) can determine that, due to the curved area 1108 of hard tissue, skiving is likely (e.g., if the target trajectory were followed). For example, the controller (such as the skiving detection module 316 (FIG. 3)) can analyze the model and determine whether the curved area 1108 is likely to cause skiving while drilling. In some embodiments, the controller uses a number of factors including diameter of the hole to be drilled, curvature at the target entry point 1106, target trajectory axis 1104, bone density, drill tip material, and/or speed of drill to make a determination. In some embodiments, the controller can definitively determine that skiving will or will not occur (e.g., if the skiving threshold is surpassed or is not surpassed). However, in some other embodiments, the controller can output a skiving risk (e.g., high risk, low risk, or a numeric or other representation of risk). If the skiving threshold is surpassed, or the skiving risk is unacceptable, the controller can determine an anti-skiving trajectory 1110. The anti-skiving trajectory 1110 can comprise one or more of an instrument size other than the target trajectory instrument size, an anti-skiving trajectory axis 1112, and an anti-skiving entry point 1114. The anti-skiving trajectory 1110 can be configured to be followed fully autonomously (e.g., entirely by the controller), manually by the surgeon, or semi-autonomously. For example, in the semi-autonomous mode, one or more virtual boundaries (e.g., a virtual fence of a given diameter or axis with a given offset) can be activated to keep the drill on the axis of the anti-skiving trajectory, and/or to prevent the user from drilling outside of the depth and or diameter that is needed for the drill point or bore (e.g., the virtual boundary can be limited in depth). The same virtual boundaries can also be used to provide haptic guidance to the user to initially locate the drill tip on the anti-skiving trajectory axis.

Figure 12:
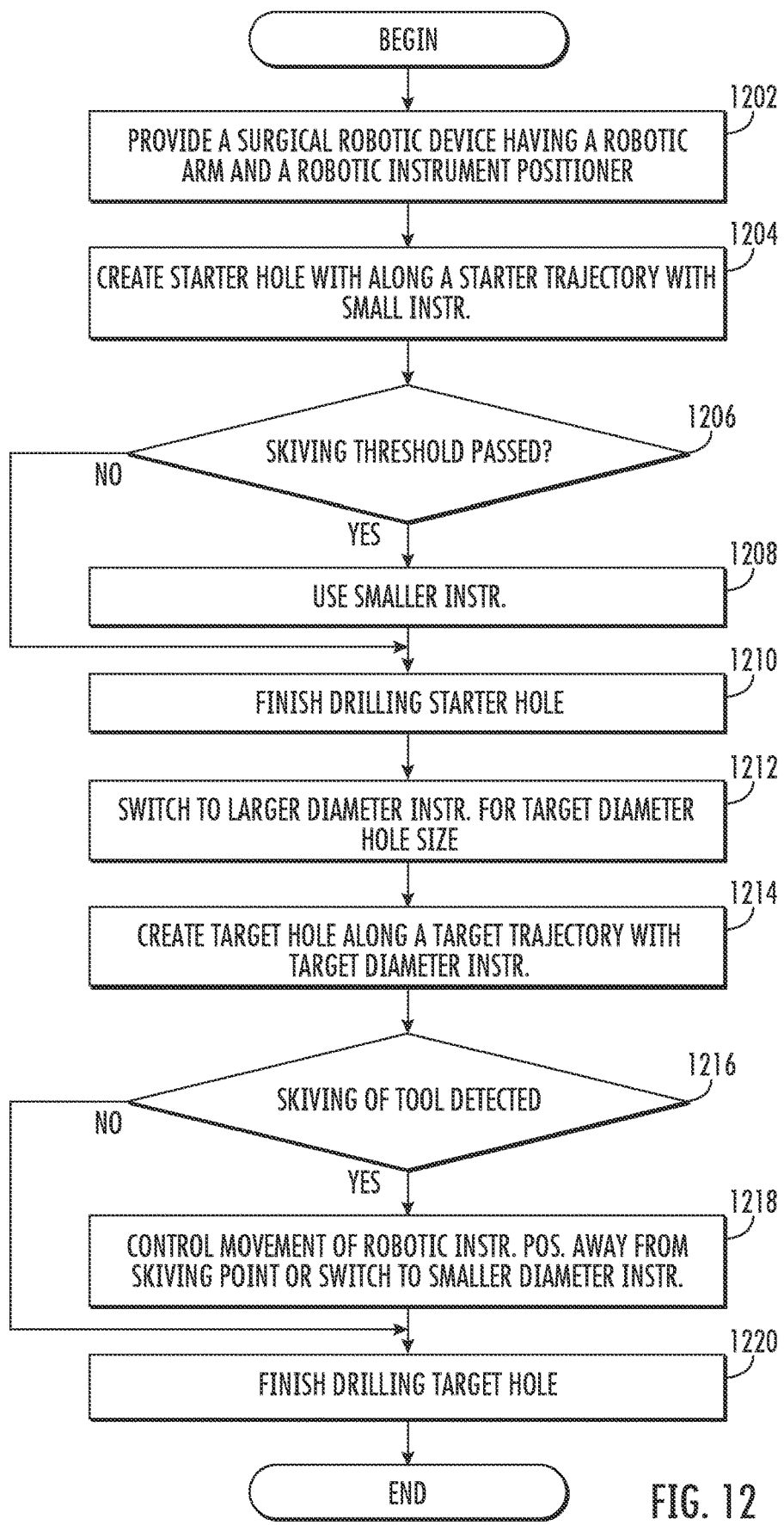
FIG. 12 is a flowchart of a method of detecting and responding to skiving of a surgical instrument.

FIG. 12 is a flowchart of one embodiment of a method of detecting skiving and responding to skiving detection. As above, portions of the flowchart are referred to as steps, but it is understood that the steps can be omitted, repeated, sub-divided, concurrently performed, or performed in a different order without departing from the spirit of the disclosure.

At step 802, a surgical robotic device having a robot arm and a robot instrument positioner attached to a distal end of the robot arm is provided. Examples of a robotic device having a robot arm were previously described at FIGS. 1&2. Example of robot instrument positioners were previously described at FIGS. 4&5.

At step 1204, a starter bore (e.g., hole) is commenced. It is understood that the hole can be along a target trajectory axis or an anti-skiving trajectory axis, but a tool attached to the robot instrument positioner is equipped with a first drilling instrument, such as a relatively smaller diameter rotary burr, cylindrical drill, etc. than was determined for creating the target trajectory's diameter. To assist with reducing the likelihood of skiving, drilling can begin with a smaller diameter burr, which can be smaller than the target hole diameter. The smaller burr can be followed by a larger burr, which can drop into the starter hole formed by the smaller burr. This iterative, sequential process can reduce the likelihood of skiving. The size of the drilling instrument can be increased step wise or sequentially, working up the ultimately desired size.

At step 1206, a determination is made as to whether a skiving threshold is passed, for example, as described previously. If the skiving threshold is not surpassed ("NO") with the given size of burr, then the process can move to step 1210. If the skiving threshold is surpassed ("YES"), at step 1208, the tool is equipped with an even smaller second drilling instrument. Alternatively, at step 1208, the tool equipped with the first drilling instrument is released from the robot instrument positioner and a second tool equipped with the second drilling instrument is attached to the robot instrument positioner. Examples of the first and second drilling instruments can comprise rotary burr drilling instruments of differing diameters (such as described with reference to FIG. 6). Additionally, at step 1208 the controller (e.g., skiving detection module 316 (FIG. 3)) can determine what maximum size burr should be used so that the skiving threshold is not passed.

In some embodiments, the robot instrument positioner, can have a high-speed compensation system. The high-speed compensation system can reduce the risk of skiving and/or be able to quickly correct skiving before too much bone is removed at a misaligned starter hole entry point relative to the target trajectory. For example, the controller can sense the burr moving off trajectory and provide an adjustment to one or more pivot points of the robot instrument positioner to correct the trajectory quickly. The controller's interface with the robot instrument positioner can be such that skiving movements can be detected in real-time or substantially instantaneously. Further, the high-speed compensation system of the robot instrument positioner can provide corrective adjustments (e.g., via one or more pivot points of the robot instrument positioner) that are smaller in magnitude, more precise, and more rapid than can be applied by the robot arm. Additionally, or alternatively, the system can shut off the burr completely and provide a warning to the surgeon for example that skiving is occurring or the starter hole is misaligned.

At step 1210, the starter hole can be finished.

At step 1212, the tool is equipped with a drilling instrument, for the target diameter hole size. Alternatively, the tool equipped with the previous drilling instrument is released from the robot instrument positioner and a tool equipped with a target diameter hole-sized drilling instrument is attached to the robot instrument positioner.

At step 1214, a target hole along the target trajectory is created.

At step 1216, as the target hole is being drilled, the controller can determine if skiving of the drilling instrument is detected. Skiving can be detected using the controller or various sensors of the robot instrument positioner and its high-speed compensation system that can quickly detect and/or counter movements of smaller magnitude than is possible using the surgical navigation system. If no skiving is detected ("NO"), the process can proceed to step 1220.

If skiving is detected ("YES") at step 1216, the process can proceed to step 1218. At step 1218, movement of the high-speed compensation of the robot instrument positioner is controlled to counter skiving. Specifically, the high-speed compensation system of the robot instrument positioner can be backed out of a skiving trajectory quickly, can be adjusted to correct a skiving trajectory toward a target trajectory, or it can cause the drilling instrument to be turned off. Additionally, the robot instrument positioner can be configured to move at speeds greater than the robot arm and, in some embodiments, can move at speeds that are one or more multiples or orders of magnitude greater than is possible with the robot arm. This is at least partly because the range of movements of the robot instrument positioner are much smaller than those of the robot arm.

At step 1220, drilling of the target hole is completed.

Examples of the above-described embodiments can include the following.

In a first example, a surgical system is provided, comprising a robot arm configured to position a tool for receiving one or more drilling instruments relative to patient anatomy, and a controller coupled to the robot arm and configured to: receive a target trajectory for drilling a hard tissue, the target trajectory having a target entry point, a target diameter, a target axis, and a target depth; analyze a three-dimensional model of the hard tissue, including a surface curvature of the hard tissue at the target entry point; determine that a skiving threshold is surpassed, wherein surpassing the skiving threshold indicates skiving is at least likely while drilling along the target orientation; and determine an anti-skiving trajectory for drilling the hard tissue before drilling the target trajectory, wherein the anti-skiving trajectory differs from the target trajectory by at least one of entry point, diameter, axis, or depth. In some embodiments, the anti-skiving trajectory differs from the target trajectory by at least one of entry point, diameter, or axis. In some embodiments, the anti-skiving trajectory differs from the target trajectory by at least one of entry point or axis. In some embodiments, the anti-skiving trajectory differs from the target trajectory by at least one of diameter or depth. In some embodiments, a drilling instrument for following the target trajectory is a pointed cylindrical drill bit. In any of the preceding embodiments, a drilling instrument for following the anti-skiving trajectory is a rotary burr. In any of the preceding embodiments, a pair of differing diameter drilling instruments for following the anti-skiving trajectory. In any of the preceding embodiments, a drilling instrument for following the target trajectory has a larger diameter than a drilling instrument for following the anti-skiving trajectory; alternatively, a drilling instrument for following the target trajectory has a smaller diameter than a drilling instrument for following the anti-skiving trajectory. In any of the preceding embodiments, the anti-skiving trajectory has an axis that is more perpendicular to the surface curvature of the hard tissue at the target entry point than an axis of the target trajectory. In any of the preceding embodiments, the system further comprises an interface for providing feedback to a user to facilitate at least partial user control of the drilling instrument. In any of the preceding embodiments, the controller is further configured to position the robot arm such that the drilling instrument is aligned with the anti-skiving trajectory. In any of the preceding embodiments, the controller is further configured to autonomously drill along the anti-skiving trajectory utilizing the anti-skiving axis and anti-skiving depth; alternatively, the controller is further configured to provide virtual boundaries to allow a user to semi-autonomously drill along the anti-skiving trajectory utilizing the anti-skiving axis and anti-skiving depth. In any of the preceding embodiments, the controller is further configured to position the robot arm such that the drilling instrument is aligned with the target trajectory after drilling along the anti-skiving trajectory. In any of the preceding embodiments, the system further comprises a robot instrument positioner interposed between the robot arm and the tool. In some embodiments, the robot instrument positioner is pivotable with respect to the robot arm to increase the adjustability of the tool's position. In some embodiments, the controller is further configured to move the robot instrument positioner if the skiving threshold is surpassed. In some embodiments, the controller is configured to move the robot instrument positioner before moving the robot arm if the skiving threshold is surpassed.

In a second example, a robot instrument positioner for a surgical tool is provided, comprising a coupler for connecting the robot instrument positioner to a robot arm of a surgical system, a guide rail for engaging the tool, and a first pivot assembly and a second pivot assembly attached to the guide rail for varying a longitudinal axis of the tool in response to a command from a controller. In some embodiments, the robot instrument positioner further comprises a quick change mechanism to releasably lock the guide rail and tool against respective movement. In any of the preceding embodiments, the robot instrument positioner further comprises an actuator to pivot one or more of the first pivot assembly and the second pivot assembly. In some embodiments, the robot instrument positioner further comprises a sensor connected to the actuator.

In a third example, a surgical method is provided, comprising receiving a target trajectory for drilling a hard tissue having a target entry point, a target orientation and a target depth, analyzing a three-dimensional model of the hard tissue using a digital data processor to determine that a surface curvature of the hard tissue at the target entry point surpasses a skiving threshold that indicates skiving is likely while drilling along the target orientation, calculating an anti-skiving trajectory using the digital data processor, the anti-skiving trajectory having an anti-skiving orientation and an anti-skiving depth that are different from the target orientation and the target depth such that the anti-skiving trajectory alters the curvature of the hard tissue at the target entry point to be below the skiving threshold while drilling along the target orientation. In some embodiments, the method further comprises creating the three-dimensional model of the hard tissue using a digital data processor via auto-segmentation of data captured by a scan of the hard tissue. In some embodiments, the scan of the hard tissue is any of an X-ray, a computerized tomography (CT), a magnetic resonance imaging (MRI), an ultrasound, an optical camera, or a coordinate measuring machine. In any of the preceding embodiments, the method further comprises drilling along the anti-skiving trajectory utilizing the anti-skiving orientation and the anti-skiving depth. In any of the preceding embodiments, the method further comprises drilling along the target trajectory utilizing the target orientation and the target depth after drilling along an anti-skiving trajectory. In any of the preceding embodiments, the method further comprises retracting a drill along the anti-skiving trajectory prior to drilling along the target trajectory. In any of the preceding embodiments, the method further comprises positioning a drill tip in a hole formed by drilling along the anti-skiving trajectory prior to drilling along the target trajectory. In any of the preceding embodiments, the method further comprises utilizing a surgical robot to control drilling along the anti-skiving trajectory. In any of the preceding embodiments, the method further comprises allowing a user at least partial control of drilling along the target trajectory. In any of the preceding embodiments, the method further comprises providing feedback to a user drilling along the target trajectory. In any of the preceding embodiments, the method further comprises using a first drilling instrument for drilling along the anti-skiving trajectory and using a second drilling instrument for drilling along the target trajectory. In some embodiments, the first drilling instrument has a diameter less than a diameter of the second drilling instrument. In some embodiments, the first drilling instrument has a diameter greater than a diameter of the second drilling instrument. In some embodiments, the first drilling instrument is a rotary burr (e.g., optionally with a convex rounded tip profile) and the second drilling instrument is a pointed cylindrical drill bit. Alternatively, the first drilling instrument has a diameter greater than a diameter of the second drilling instrument (e.g., to form a flat). In any of the preceding embodiments, the method further comprises providing an axis of the anti-skiving trajectory to contact the entry point at an angle that is closer to perpendicular to the surface of the hard tissue than the target orientation. In any of the preceding embodiments, the method further comprises determining to drill the anti-skiving depth at less than the target depth.

The invention claimed is:

1. A surgical system, comprising:
a robot arm configured to position a tool for receiving one or more drilling instruments relative to patient anatomy; and
a controller coupled to the robot arm and configured to:
receive a target trajectory for drilling a hard tissue, the target trajectory having a target entry point, a target diameter, a target axis, and a target depth;
analyze a three-dimensional model of the hard tissue, including a surface curvature of the hard tissue at the target entry point;
determine that a skiving threshold is surpassed, wherein surpassing the skiving threshold indicates skiving is at least likely while drilling along a target orientation; and
determine an anti-skiving trajectory for drilling the hard tissue before drilling the target trajectory, wherein the anti-skiving trajectory differs from the target trajectory by at least one of entry point, diameter, axis, or depth.

2. The system of claim 1, wherein the one or more drilling instruments is a pointed cylindrical drill bit for following the target trajectory.

3. The system of claim 1, wherein the one or more drilling instruments is a rotary burr for following the anti-skiving trajectory.

4. The system of claim 3, wherein the one or more drilling instruments is a pair of differing rotary burrs.

5. The system of claim 1, wherein the one or more drilling instruments includes a drilling instrument for following the target trajectory and a drilling instrument for following the anti-skiving trajectory, wherein the drilling instrument for following the target trajectory has a larger diameter than the drilling instrument for following the anti-skiving trajectory.

6. The system of claim 1, wherein the one or more drilling instruments includes a drilling instrument for following the target trajectory and a drilling instrument for following the anti-skiving trajectory, wherein the drilling instrument for following the target trajectory has a smaller diameter than the drilling instrument for following the drilling instrument for following the anti-skiving trajectory.

7. The system of claim 1, wherein the anti-skiving trajectory has an axis that is more perpendicular to the surface curvature of the hard tissue at the target entry point than an axis of the target trajectory.

8. The system of claim 1, further comprising an interface for providing feedback to a user to facilitate at least partial user control of the drilling instrument.

9. The system of claim 1, wherein the controller is further configured to position the robot arm such that the drilling instrument is aligned with the anti-skiving trajectory.

10. The system of claim 9, wherein the controller is further configured to autonomously drill along the anti-skiving trajectory utilizing an anti-skiving axis and anti-skiving depth.

11. The system of claim 10, wherein the controller is further configured to position the robot arm such that the drilling instrument is aligned with the target trajectory after drilling along the anti-skiving trajectory.

12. The system of claim 9, wherein the controller is further configured to provide virtual boundaries to allow a user to semi-autonomously drill along the anti-skiving trajectory utilizing the anti-skiving axis and anti-skiving depth.

13. The system of claim 1, further comprising a robot instrument positioner configured to be interposed between the robot arm and the tool.

14. The system of claim 13, wherein the robot instrument positioner is pivotable with respect to the robot arm to increase adjustability of the tool's position.

15. The system of claim 14, wherein the controller is further configured to move the robot instrument positioner if the skiving threshold is surpassed.

16. The system of claim 15, wherein the controller is further configured to move the robot instrument positioner before moving the robot arm if the skiving threshold is surpassed.

17. The system of claim 13, wherein the robot instrument positioner comprises:
a coupler for connecting the robot instrument positioner to the robot arm;
a guide rail for engaging the tool; and
a first pivot assembly and a second pivot assembly attached to the guide rail for varying a longitudinal axis of the tool in response to a command from the controller.

18. The system of claim 17, further comprising a quick-change mechanism to releasably lock the guide rail and tool against respective movement.

19. The system of claim 17, further comprising an actuator to pivot one or more of the first pivot assembly and the second pivot assembly.

20. The system of claim 19, further comprising at least one of a force sensor or a deflection sensor operably connected to the actuator.

\* \* \* \* \*